(12) United States Patent
Suzuki et al.

(10) Patent No.: US 6,870,069 B2
(45) Date of Patent: Mar. 22, 2005

(54) PHENYLOXYANILINE DERIVATIVES

(75) Inventors: Kazutoshi Suzuki, Chiba (JP); Ming-Rong Zhang, Chiba (JP); Tetsuya Suhara, Chiba (JP); Atsuro Nakazato, Tokyo (JP); Makoto Goto, Tokyo (JP)

(73) Assignees: National Institute of Radiological Sciences, Chiba (JP); Taisho Pharmaceutical Co., Ltd., Tokyo (JP); Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 10/699,743

(22) Filed: Nov. 4, 2003

(65) Prior Publication Data

US 2004/0138310 A1 Jul. 15, 2004

(30) Foreign Application Priority Data

Jan. 10, 2003 (JP) .................................... P.2003-004251

(51) Int. Cl.[7] ........................ C07C 233/05; A61K 31/16
(52) U.S. Cl. ........................ 564/221; 564/218; 564/219; 514/628; 514/630
(58) Field of Search ................. 564/218, 219, 564/221; 514/628, 630

(56) References Cited

U.S. PATENT DOCUMENTS 6,333,358 B1 * 12/2001 Nakazato et al. ........... 514/650

FOREIGN PATENT DOCUMENTS

JP     11-171844 A     6/1999

OTHER PUBLICATIONS

Zhang et al, Bioorganic & Medicinal Chemistry Letters, 13 (2003) 201–204.*
Zhang et al, "Radiosynthesis and Evaluation PET Tracers for Peripheral Benzodiazephine Receptor (PBR)" 22nd Symposium on Medicinal Chemistry (11th Annual Meeting of Division of Medicinal Chemistry (Nov. 5, 2002).

* cited by examiner

Primary Examiner—Shailendra Kumar
(74) Attorney, Agent, or Firm—Sughrue Mion, PLLC

(57) ABSTRACT

A phenyloxyaniline derivative useful as a ligand for peripheral benzodiazepine receptor having a strong affinity and a high selectivity, which is represented by formula (1):

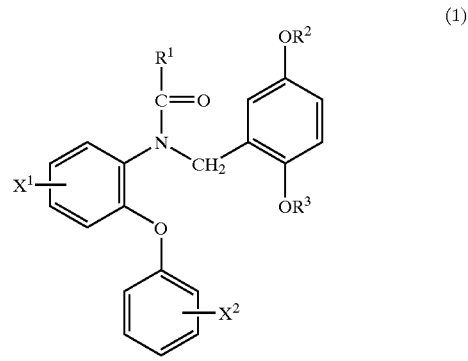

wherein $X^1$ and $X^2$ are same or different and each is hydrogen atom or halogen atom; $R^1$ and $R^2$ are same or different and each is hydrogen atom, an alkyl group having 1 to 10 carbon(s) or a halogen-substituted alkyl group having 1 to 10 carbon(s); and $R^3$ is a halogen-substituted alkyl group having 1 to 5 carbon(s), or a radioisotope thereof.

7 Claims, No Drawings

PHENYLOXYANILINE DERIVATIVES

FIELD OF THE INVENTION

The present invention relates to a compound having a high affinity to a peripheral benzodiazepine receptor.

BACKGROUND OF THE INVENTION

Benzodiazepine (BZ) receptors are classified into central and peripheral benzodiazepine receptors. A peripheral benzodiazepine receptor (PBR) was at first confirmed in the periphery but its presence in the central nervous system was noted as well. It has been further clarified that PBR has a high density in the central nervous system and the density is same as or even higher than that of a central benzodiazepine receptor (CBR) in the same region. According to recent studies, it has been reported that PBR is present in microglia cells in the brain and increases in psychoneural diseases such as Alzheimer's disease where microglia is activated in the brain.

In a $^{11}$C-labeled substance of N-methyl-N-(1-methylpropyl)-1-(2-chlorophenyl)-isoquinoline-3-carboxamide (hereinafter, referred to as PK11195) which is a conventional PBR ligand, its usefulness in diagnosis of glioma in the brain and Alzheimer's disease has been reported. However, its accumulation to the brain is very low and there is a problem for a quantitative analysis. In an image processing of distribution of PBR in a living human brain using a positron emission tomograph (PET), there is a demand for the development of a PBR ligand being able to obtain a high signal and, since N-(2,5-dimethoxybenzyl)-N-(5-fluoro-2-phenoxyphenyl)acetamide (hereinafter, referred to as DAA1106) (JP-A-11-171844, the term "JP-A" as used herein means an "unexamined published Japanese patent application") has a strong affinity and a high selectivity, it has been known to be suitable for such an object.

SUMMARY OF THE INVENTION

An object of the present invention is to provide a compound which is useful as a ligand for PBR having a strong affinity and a high selectivity and, in an external measurement of PBR where a sufficient signal has not been obtained until now, to label a ligand of PBR having a high affinity and a high selectivity with a positron nuclide whereby measurement of PBR in a living body is made possible. As a result, an early diagnosis of central diseases such as integration dysfunction syndrome, depression, epilepsy and Alzheimer's disease is able to be made possible. Another object is to provide a drug having a high affinity to PBR which is effective to symptoms being unable to achieve a satisfactory therapeutic effect by the conventional BZ substances, does not show side effect such as an excessive sedation or psychological dependence being noted in the BZ substances and shows treating and preventive effects for central diseases including anxiety and related diseases such as depression and epilepsy.

As a result of extensive investigations and studies to solve the above-mentioned problems, the present inventors have found that, when an alkyl group of the compound mentioned in JP-A-11-171844 is made into a halogenated alkyl group, a quite good PBR affinity is achieved whereupon the present invention has been achieved.

That is, the present invention provides a phenyloxyaniline derivative represented by formula (1):

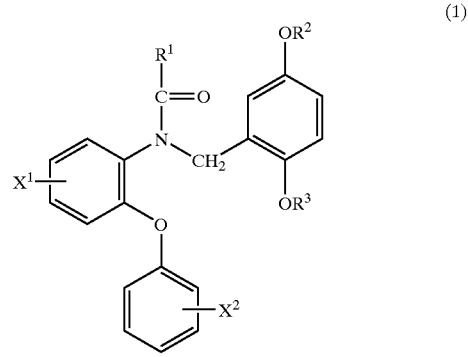

(1)

wherein $X^1$ and $X^2$ are same or different and each is a hydrogen atom or a halogen atom; $R^1$ and $R^2$ are same or different and each is a hydrogen atom, an alkyl group having 1 to 10 carbon(s) or a halogen-substituted alkyl group having 1 to 10 carbon(s); and $R^3$ is a halogen-substituted alkyl group having 1 to 5 carbon(s), or a radioisotope thereof.

The present invention also relates to a phenyloxyaniline derivative represented by formula (2):

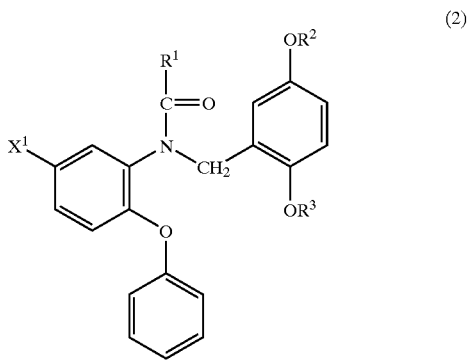

(2)

wherein $X^1$ is a hydrogen atom or a halogen atom; $R^1$ and $R^2$ are same or different and each is a hydrogen atom, an alkyl group having 1 to 10 carbon(s) or a halogen-substituted alkyl group having 1 to 10 carbon(s); and $R^3$ is a halogen-substituted alkyl group having 1 to 5 carbon(s), or a radioisotope thereof.

Another feature of the present invention relates to the use of the above-mentioned phenyloxyaniline derivative or a radioisotope thereof as a peripheral benzodiazepine receptor labeling ligand.

DETAILED DESCRIPTION OF THE INVENTION

In the present invention, the halogen atom is a fluorine atom, a chlorine atom, a bromine atom or an iodine atom. The halogen atom in $R^3$ is preferably a fluorine atom, an iodine atom or a bromine atom and, more preferably, a fluorine atom or an iodine atom.

The alkyl group having 1 to 10 carbon(s) means a linear or branched alkyl group and its examples are a methyl group, an ethyl group, an n-propyl group, an isopropyl group, an n-butyl group and an n-heptyl group.

The halogen-substituted alkyl group having 1 to 10 carbon(s) means a linear or branched alkyl group where 1 to 3 halogen atom(s) is/are substituted for a hydrogen atom(s) and, preferably, it is an alkyl group substituted with fluorine or iodine atom(s). Examples thereof are a fluoromethyl group, a 2-fluoroethyl group, an 2-iodoethyl group, a 5-fluoroheptyl group and a 6-bromohexyl group. The halogen-substituted alkyl group having 1 to 5 carbon(s) means a linear or branched alkyl group where 1 to 3 halogen atom(s) is/are substituted for a hydrogen atom(s) and, preferably, it is an alkyl group substituted with fluorine or iodine atom(s). Examples thereof area fluoromethyl group, a 2-fluoroethyl group, an 2-iodoethyl group and a 5-fluoroheptyl group.

The radioisotope in the present invention means that where atom(s) contained in the formula (1) is/are substituted with radioisotope(s). Thus, at least one atom of carbon atoms and halogen atoms in the alkyl group defined by $X^1$, $X^2$, $R^1$, $R^2$ and $R^3$ is substituted with a radioisotope and that which is substituted with $^{11}C$, $^{18}F$, $^{123}I$ or the like may be exemplified.

The compound of the present invention is able to be produced according to a process mentioned by the following reaction formulae starting from a compound produced by the same manner as described in JP-A-11-171844, the text of which is incorporated herein by reference. (In the reaction formulae, Bz is a benzyl group and $X^1$, $X^2$ $R^1$, $R^2$ and $R^3$ are the same as those defined above.)

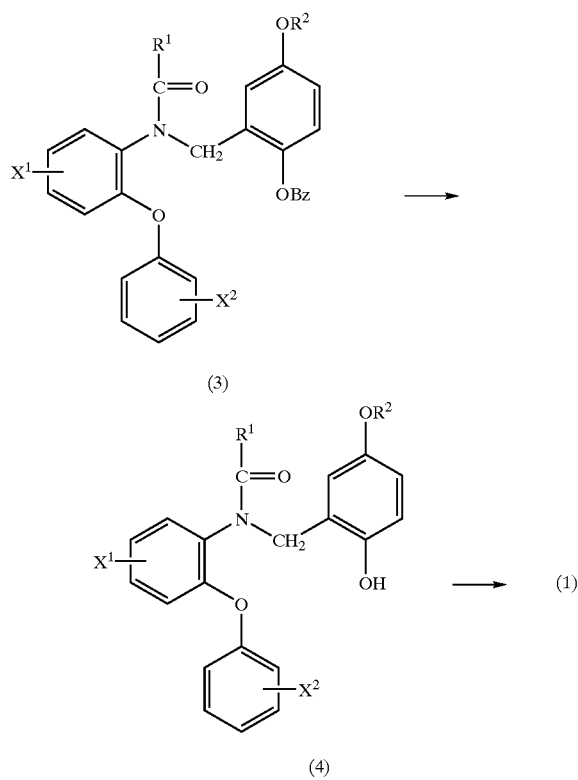

(3)

(4)

That is, an N-(2-benzyloxy-5-alkoxybenzyl)-N-(phenoxyphenyl)acylamide compound represented by the formula (3) is converted to an N-(2-hydroxy-5-alkoxybenzyl)-N-(phenoxyphenyl)acylamide compound represented by the formula (4) by removing the benzyl group by means of reduction or the like and then it is made to react with a compound of the formula $R^3$—X (wherein $R^3$ has the same meaning as defined above and X is a leaving group in an alkylation) in the presence or the absence of a base whereupon the product can be easily produced. Examples of the leaving group in the alkylation are a halogen atom such as iodine and bromine and a sulfonyl group such as a toluenesulfonyl group, a p-toluenesulfonyl group and a methanesulfonyl group. The base is an organic amine such as triethylamine, diisopropylamine and pyridine; an inorganic base such as potassium carbonate, sodium hydroxide, sodium hydride and metal sodium; metal alcoholate such as sodium methoxide and potassium tert-butoxide; or the like.

EXAMPLES

The present invention will now be illustrated in more detail by way of the following Examples.

Example 1

Production of N-(2-fluoromethyl-5-methoxybenzyl)-N-(5-fluoro-2-phenoxyphenyl)acetamide (hereinafter, referred to as FMDAA1106)

An oily sodium hydride (60%) (5.1 mg) was added to a solution of N-(2-hydroxy-5-methoxybenzyl)-N-(5-fluoro-2-phenoxyphenyl)acetamide (hereinafter, referred to as DAA1123) (18 mg) in N,N-dimethylformamide (DMF; 1.0 mL) followed by stirring at 0° C., 10 mg of fluoromethyl iodide ($FCH_2I$) were added thereto and the mixture was further stirred at 0° C. for 1 hour. Water was added to the reaction solution, the mixture was extracted with ethyl acetate and the organic layer was washed with saturated brine and dried over anhydrous magnesium sulfate. The solvent was evaporated under reduced pressure and the resulting crude product was purified by a silica gel column chromatography (chloroform:hexane:ethyl acetate=1:3:1) to give 16 mg of the above-identified compound.

Melting point: 71 to 72° C.

Example 2

Production of N-(2-[$^{18}F$]fluoromethyl-5-methoxybenzyl-N-(5-fluoro-2-phenoxyphenyl)acetamide (hereinafter, referred to as [$^{18}F$]FMDAA1106)

[$^{18}F$]fluorine ([$^{18}F$]F) was produced by irradiation of 18 MeV proton using 20 atom.% $H_2^{18}O$. After the irradiation, [$^{18}F$]F$^-$ was recovered from a target, separated from [$^{18}O$]$H_2O$ by an anion-exchange resin Dowex 1-X8, mixed with acetonitrile ($CH_3CN$, 1.5 mL) containing Kryptofix 2.2.2. (25 mg) and transferred from an irradiation chamber to a synthetic cell. After [$^{18}F$]F was dried in a synthetic cell, diiodomethane ($CH_2I_2$) was injected into a reactor at 130° C. Together with the injection, [$^{18}F$]F $CH_2I$ produced by helium gas was bubbled into a solution of 1 mg of DAA1123 and sodium hydride (6.8 μL, 0.5 g/20 mL) in DMF (300 mL). After this process was maintained at room temperature for 10 minutes, the reaction mixture was injected into a reversed phase semi-separation HPLC (YMCJ' sphere ODS-H80 column; 10 mm ID×250 mm). A fraction of [$^{18}F$] FMDAA1106 was collected where the mobile phase was $CH_3CN/H_2O$ at the flow rate of 6 mL/minute. The solvent was evaporated under reduced pressure from this fraction and the residue was dissolved in saline (10 mL) and passed through a 0.22-μm Millipore filter to give [$^{18}$F] FMDAA1106 (110 MBq, n=3) as the final preparation. (Condition for irradiation; 15 minutes, 15 μA). Incidentally, the synthetic time needed was about 45 minutes from the completion of the irradiation.

Example 3

Production of N-[2-(2-fluoro)ethyl-5-methoxybenzyl]-N-(5-fluoro-2-phenoxyphenyl)acetamide (hereinafter, referred to as FEDAA1106)

The same operation as in Example 1 was carried out where 1-fluoro-2-tosyloxyethane ($FCH_2CH_2OTs$) was used instead of fluoromethyl iodide ($FCH_2I$) to give 20 mg of the above-identified compound.

Melting point: 54 to 56° C.

Example 4

Production of N-[2-(2-[$^{18}$F]fluoro)ethyl-5-methoxybenzyl]-N-(5-fluoro-2-phenoxyphenyl)acetamide (hereinafter, referred to as [$^{18}$F]FEDAA1106)

The same operation as in Example 2 was carried out where 2-bromoethyl triflate ($BrCH_2CH_2OTf$) was used instead of diiodomethane ($CH_2I_2$) to give the above-identified compound.

Test Example

Affinity to PBR in vitro was investigated according to the conventional methods mentioned in Sihver, S., et al.: *J. Pharmacol. Exp. Ther.* 1999, 290, 917 and Zhang, M.-R., et al.: *Nucl. Med. Biol.*, 2002, 29, 469.

Under anesthetization with ether, male Sprague-Dawley rats (250 to 300 g; n=4) were slaughtered and the brain was quickly cut and frozen in dry ice. Sagittal sections of the rat were prepared using Crystat microtome (MICROM HM560, Carl Zeiss GmbH, Germany). The sections were previously incubated in a 50 mM Tris buffer (pH=7.4) for 30 minutes. After that, the sections were taken out and again incubated at 37° C. for 30 minutes in 50 mM Tris buffer (pH=7.4) containing each of the following reagents at the same time. Reagents:

1. [$^{11}$C]DAA1106 (1 nM)
2. [$^{11}$C]DAA1106 (1 nM)+DAA1106 (0.1 nM)
3. [$^{11}$C]DAA1106 (1 nM)+DAA1106 (0.33 nM)
4. [$^{11}$C]DAA1106 (1 nM)+DAA1106 (1 nM)
5. [$^{11}$C]DAA1106 (1 nM)+DAA1106 (3.3 nM)
6. [$^{11}$C]DAA1106 (1 nM)+DAA1106 (10 nM)
7. [$^{11}$C]DAA1106 (1 nM)+DAA1106 (33 nM)
8. [$^{11}$C]DAA1106 (1 nM)+DAA1106 (100 nM)
9. [$^{11}$C]DAA1106 (1 nM)+DAA1106 (1 μM)
10. [$^{11}$C]DAA1106 (1 nM)+DAA1106 (10 μM)
11. [$^{11}$C]DAA1106 (1 nM)+PK11195 (0.1 nM)
12. [$^{11}$C]DAA1106 (1 nM)+PK11195 (0.33 nM)
13. [$^{11}$C]DAA1106 (1 nM)+PK11195 (1 nM)
14. [$^{11}$C]DAA1106 (1 nM)+PK11195 (3.3 nM)
15. [$^{11}$C]DAA1106(1 nM)+PK11195 (10 nM)
16. [$^{11}$C]DAA1106 (1 nM)+PK11195 (33 nM)
17. [$^{11}$C]DAA1106 (1 nM)+PK11195 (100 nM)
18. [$^{11}$C]DAA1106 (1 nM)+PK11195 (1 μM)
19. [$^{11}$C]DAA1106 (1 nM)+PK11195 (10 μM)
20. [$^{11}$C]DAA1106 (1 nM)+FMDAA1106 (0.1 nM)
21. [$^{11}$C]DAA1106 (1 nM)+FMDAA1106 (0.33 nM)
22. [$^{11}$C]DAA1106 (1 nM)+FMDAA1106 (1 nM)
23. [$^{11}$C]DAA1106 (1 nM)+FMDAA1106 (3.3 nM)
24. [$^{11}$C]DAA1106 (1 nM)+FMDAA1106 (10 nM)
25. [$^{11}$C]DAA1106 (1 nM)+FMDAA1106 (33 nM)
26. [$^{11}$C]DAA1106 (1 nM)+FMDAA1106 (100 nM)
27. [$^{11}$C]DAA1106 (1 nM)+FMDAA1106 (1 μM)
28. [$^{11}$C]DAA1106 (1 nM)+FMDAA1106 (10 μM)
29. [$^{11}$C]DAA1106 (1 nM)+FEDAA1106 (0.1 nM)
30. [$^{11}$C]DAA1106 (1 nM)+FEDAA1106 (0.33 nM)
31. [$^{11}$C]DAA1106 (1 nM)+FEDAA1106 (1 nM)
32. [$^{11}$C]DAA1106 (1 nM)+FEDAA1106 (3.3 nM)
33. [$^{11}$C]DAA1106 (1 nM)+FEDAA1106 (10 nM)
34. [$^{11}$C]DAA1106 (1 nM)+FEDAA1106 (33 nM)
35. [$^{11}$C]DAA1106 (1 nM)+FEDAA1106 (100 nM)
36. [$^{11}$C]DAA1106 (1 nM)+FEDAA1106 (1 μM)
37. [$^{11}$C]DAA1106 (1 nM)+FEDAA1106 (10 μM)

After completion of the incubation, the section was taken out and dipped in an ice-cooled Tris buffer for 2 minutes twice. The section was dipped in ice-cooled distilled water and then dried. The above section was contacted for 1 hour to an imaging plate (BAS-SR 127, manufactured by Fuji Photo Film) and then distribution of radioactivity on the section was determined by FUJIX BAS 1800 bioimaging analyzer (manufactured by Fuji Photo Film). A region of interest (ROI) was defined as an olfactory bulb and radioactivity was expressed in terms of a photo-stimulated-luminescence (PSL)/mm$^2$ region. Specific binding of [$^{11}$C] DAA1106 in the presence of DAA1106, PK11156, FMDAA1106 and FEDAA1106 of various concentrations was determined and $IC_{50}$ (nM) of those reagents was calculated by a probit method.

The result is shown in Table 1. As shown in Table 1, FEDAA1106 showed a two-fold higher affinity to PBR as compared with DAA1106. On the other hand, FMDAA1106 showed the similar affinity as DAA1106. As a result, fluoroethyl group instead of methoxy group caused an enhancement of affinity and fluoromethyl group did not affect the affinity. In addition, FEDAA1106 showed about ten-fold stronger affinity as compared with the most frequently used PK11195. On the other hand, affinity of FMDAA1106 and FEDAA1106 to central benzodiazepine receptor (CBR) was determined (Table 1) using [$^{11}$C]flumazenil which is a selective ligand for CBR. As a result, affinity of FEDAA1106 and FMDAA1106 to CBR was not less than 10 μM and was about 10,000-fold weaker than the affinity of PBR. From the above result, although FEDAA1106 and FMDAA1106 showed a strong affinity to PBR, they almost did not show an affinity to CBR. Incidentally, partition coefficients (log P) of the two ligands were measured by an octanol/water (pH 7.4) partition method.

TABLE 1

| Reagent | $IC_{50}$(nM) PBR | $IC_{50}$(nM) CBR | log P |
|---|---|---|---|
| FMDAA1106 | 1.71 | >10,000 | 3.70 |
| FEDAA1106 | 0.77 | >10,000 | 3.81 |
| DAA1106 | 1.62 | >10,000 | 3.65 |
| PK11195 | 8.26 | >10,000 | — |

In accordance with the present invention, there is provided a compound which is useful as a ligand for PBR having a strong affinity and a high selectivity. In an external measurement of PBR where a sufficient signal has not been obtained until now, a ligand of PBR having a high affinity and a high selectivity is labeled with a positron nuclide whereby measurement of PBR in a living body is now possible. As a result, an early diagnosis of central diseases such as schizophrenia syndrome, depression, epilepsy and Alzheimer's disease is now possible.

The compound of the present invention is also useful as a treating agent for sleeping disorder, dyskinesia accompanied by muscle rigidity, feeling disorder, circulation disorder, recognition and learning disability, drug dependence, cancer, lipid metabolism abnomality, schizophrenia, cerebral infarction, AIDS, Alzheimer's disease, Huntington chorea, etc.

While the invention has been described in detail and with reference to specific examples thereof, it will be apparent to one skilled in the art that various changes and modifications can be made therein without departing from the spirit and scope thereof.

What is claimed is:

1. A phenyloxyaniline derivative represented by formula (1):

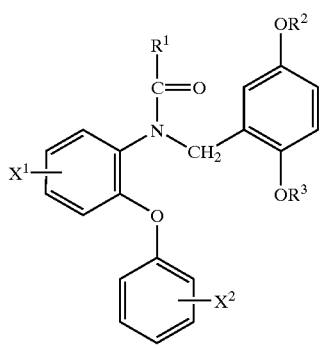

wherein $X^1$ and $X^2$ are same or different and each is a hydrogen atom or a halogen atom; $R^1$ and $R^2$ are same or different and each is a hydrogen atom, an alkyl group having 1 to 10 carbon(s) or a halogen-substituted alkyl group having 1 to 10 carbon(s); and $R^3$ is a halogen-substituted alkyl group having 1 to 5 carbon(s), or a radioisotope thereof.

2. A phenyloxyaniline derivative represented by formula (2):

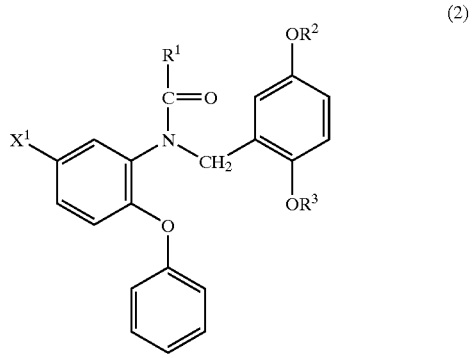

wherein $X^1$ is a hydrogen atom or a halogen atom; $R^1$ and $R^2$ are same or different and each is a hydrogen atom, an alkyl group having 1 to 10 carbon(s) or a halogen-substituted alkyl group having 1 to 10 carbon(s); and $R^3$ is a halogen-substituted alkyl group having 1 to 5 carbon(s), or a radioisotope thereof.

3. The phenyloxyaniline derivative or a radioisotope thereof according to claim 1 or 2, wherein the halogen atom is a fluorine atom, an iodine atom or a bromine atom.

4. A method of labeling a peripheral benzodiazepine receptor comprising contacting a specimen containing the peripheral benzodiazepine receptor with the phenyloxyaniline derivative or a radioisotope thereof of claim 1 or 2.

5. A method of labeling a peripheral benzodiazepine receptor comprising contacting a specimen containing the peripheral benzodiazepine receptor with the phenyloxyaniline derivative or a radioisotope thereof of claim 3.

6. A method of labeling a peripheral benzodiazepine receptor comprising administering to a subject an effective amount of the phenyloxyaniline derivative or a radioisotope thereof of claim 1 or 2.

7. A method of labeling a peripheral benzodiazepine receptor comprising administering to a subject an effective amount of the phenyloxyaniline derivative or a radioisotope thereof of claim 3.

* * * * *